US005788871A

United States Patent [19]
Huh

[11] Patent Number: 5,788,871
[45] Date of Patent: Aug. 4, 1998

[54] ETCH-ENDING POINT MEASURING METHOD FOR WET-ETCH PROCESS

[75] Inventor: Yun Jun Huh, Chungcheongbuk-do, Rep. of Korea

[73] Assignee: LG Semicon Co., Ltd., Chungcheongbuk-Do, Rep. of Korea

[21] Appl. No.: 633,018

[22] Filed: Apr. 16, 1996

[30] Foreign Application Priority Data

Dec. 26, 1995 [KR] Rep. of Korea .......... 1995 56309

[51] Int. Cl.$^6$ .................. C23F 1/00; C25F 3/00
[52] U.S. Cl. .................. 216/84; 216/83; 216/97; 216/99; 438/745
[58] Field of Search .................. 156/626.1, 662.1; 216/83, 84, 97, 99; 438/745

[56] References Cited

U.S. PATENT DOCUMENTS 3,923,567 12/1975 Lawrence .................. 438/4
5,329,124 7/1994 Yamamoto .................. 250/367

FOREIGN PATENT DOCUMENTS 1-236633 9/1989 Japan .................. H01L 21/306

OTHER PUBLICATIONS

Masterton et al., "Chemical Principles with Qualitative Analysis", p. 457, 1978.

*Primary Examiner*—Bernard P. Codd
*Attorney, Agent, or Firm*—Morgan, Lewis & Bockius LLP

[57] ABSTRACT

A wet-etching method which determines a desired etch-ended point includes the steps of providing an etchant solution in a bath, performing the wet-etch process by dipping a material to be etched in the bath, measuring a weight variation value of the material during the wet etch process, calculating a thickness variation value of the material by using the weight variation value, and stopping the wet-etch process when the thickness variation value reaches a preset value.

21 Claims, 1 Drawing Sheet

ETCH-ENDING POINT MEASURING METHOD FOR WET-ETCH PROCESS

BACKGROUND OF THE INVENTION

1. Field of the Invention

The present invention relates to a method for measuring an etch-ending point, and more particularly, to a method for measuring an etch-ending point during a wet etch process.

2. Discussion of the Related Art

An etching process is usually carried out for forming a variety of patterns during a semiconductor device manufacturing process. It can be used to etch a semiconductor layer, an insulating layer, or a conductive layer. Conventionally, etching processes are classified into processes using either a dry etch method or a wet etch method.

For both the dry etch and the wet etch methods, one important factor is the ability to decide when a layer subjected to etching has been etched to the desired thickness. In order to assure the success of the semiconductor device manufacturing process which requires minute patterns, it is essential to be able to decide accurately when each of the layers subjected to etching has been etched to the desired thickness during the etch process for forming the respective patterns. In other words, it is essential to accurately measure an etch-ending point during an etch process.

The conventional methods for measuring an etch-ending point will now be described for both the dry etch process and the wet etch process.

For the dry etch process, the widely adopted etch-ending point measuring method is a light wavelength method. When the dry etch of a silicon oxide layer ($SiO_2$) is performed by using an etchant $CF_4$, the etchant $CF_4$ reacts to the silicon oxide layer to produce a by-product such as $CO_yF_x$. A light beam, such as laser, is then projected upon the silicon oxide layer which is reacting with the etchant $CF_4$. When the light is reflected from the silicon oxide layer and the by-product resulting from the reaction, the intensity of the reflected light at specific wavelengths will vary in accordance with the degree of etching completed of the silicon oxide layer. The intensity of the reflected light at a specific wavelength is measured during the etch process and compared to a certain pre-determined intensity value set by prior experiments. Thus, when the measured intensity of the light is equal to the pre-determined intensity value set by prior experiments. Thus, when the measured intensity of the light is equal to the pre-determined intensity value, the etch-ending point has been reached.

The above-described light wavelength method for measuring the etch-ending point is also used in conventional chemical-mechanical polishing (CMA) process. The CMA process etches a layer to a desired thickness by milling the layer subjected to the etch process.

For the wet etch process, three conventional methods for measuring the etch-ending point are often used. For the purpose of discussion, it is assumed that an insulating layer is wet-etched to form a desired pattern in a structure having the insulating layer on a semiconductor layer.

The first method is a color method. After putting this structure into a bath filled with an etchant and conducting the wet etch for a period of time, the resultant structure is taken out of the bath to determine the etch-ending point by examining the surface color of the resultant structure. If the insulating layer is etched to the desired thickness, the surface color of the structure would differ from that before conducting the etch, because the color of the underlying semiconductor layer is different from that of the insulating layer.

This color method is mainly used in a partial etch process. For example, it is used when the insulating layer is etched a thickness of 4000 Å–5000 Å only.

The second method is a surface tension method. A structure comprised of a semiconductor layer, such as silicon, and an insulating layer is put in a bath filled with a wet-etchant and subjected to the wet etch. Then, the resultant structure is taken out of the bath and the surface is sprayed with water. If the insulating layer is thoroughly etched, the surface of the silicon would be exposed. Accordingly, the silicon surface may be slightly stained with the water due to the surface tension of the silicon. If the insulating layer is not thoroughly etched, the sprayed water does not adhere to the surface, instead it flows over the surface. Thus, the etch-ending point can be measured.

The third method for determining the etch-ending point uses a thickness meter. Initially, a structure comprised of a semiconductor layer and an insulating layer is put into the bath and subjected to the wet etch for a period of time. Then, the resultant structure is taken out of the bath, and the thickness of the structure is measured by using a thickness meter. If the insulating layer is thoroughly etched, the measured thickness of the structure equals the thickness of the semiconductor layer. If the insulating layer is not thoroughly etched, the measured thickness of the structure would be larger than the thickness of the semiconductor layer.

All three etch-ending point measuring methods for the wet etch process are visual methods, which can be difficult to apply when the structure has patterns. Since the etch process employed for manufacturing semiconductor devices is frequently used to form patterns, and the patterns are often of a minute nature, it is almost impossible to visually measure the etch-ending point under those circumstances.

Conventionally, in order to actually apply the above-described methods during the manufacturing process of the semiconductor devices, a test pattern with an enlarged configuration is utilized. In other words, the same manufacturing process is simultaneously performed upon the test pattern when the process is used to manufacture the semiconductor devices. The test pattern is a considerable enlargement of the actual structure, so that the above three etch-ending point measuring methods can be applied. The etch-ending point of the actual structure can be only estimated by using the color, surface tension, and thickness of the test pattern.

This technique of using the etch-ending point on the test pattern to provide an estimation for the etch-ending point of the actual structure has several problems. First, it has an inherent risk of inaccuracy of the etch-ending point for the actual structure, and such inaccuracy usually causes failures of the manufacturing process.

In addition, due to the large size of the test pattern involved and the large amount of the chemical material (such as the etchants) required, the whole manufacturing process becomes very complicated and expensive.

Furthermore, the structure is taken out of the bath one by one to either determine the color and surface tension, or measure the thickness with the meter, thereby increasing the processing time. Usually, the processing time using the conventional methods is similar to that required for wet-etching a material with a thickness corresponding to 150–200% of the thickness of a target material.

Therefore, the conventional etch-ending point measuring methods for the wet etch process are not as effective in various aspects as the measuring method for the dry etch process. However, during the manufacturing process of the semiconductor devices, it is well known that the wet etch is preferred to the dry etch under certain circumstances. Consequently, an effective etch-ending point measuring method for the wet etch process is needed.

SUMMARY OF THE INVENTION

Accordingly, the present invention is directed to an etch-ending point measuring method that substantially obviates one or more of the problems, limitations, and disadvantages of the related art.

An object of the present invention is to provide an etch-ending point measuring method with reduced risk of failure and lower financial cost. Another object of the present invention is to provide an etch-ending point measuring method which can be performed within a shorter period of time compared to the conventional method.

Additional features and advantages of the invention will be set forth in the description which follows, and in part will be apparent form the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, the etch-ending point measuring method of the present invention includes the steps of providing an etchant solution into the bath for putting a material subjected to the etch in the bath to perform the wet-etch operation, measuring a weight variation amount of the material while the set etch is performed, calculating a thickness variation amount of the material to be etched by means of the measured weight variation amount, and determining a state that the calculated thickness variation amount reaches a preset thickness variation value as an etch-ending point.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Figure 1:
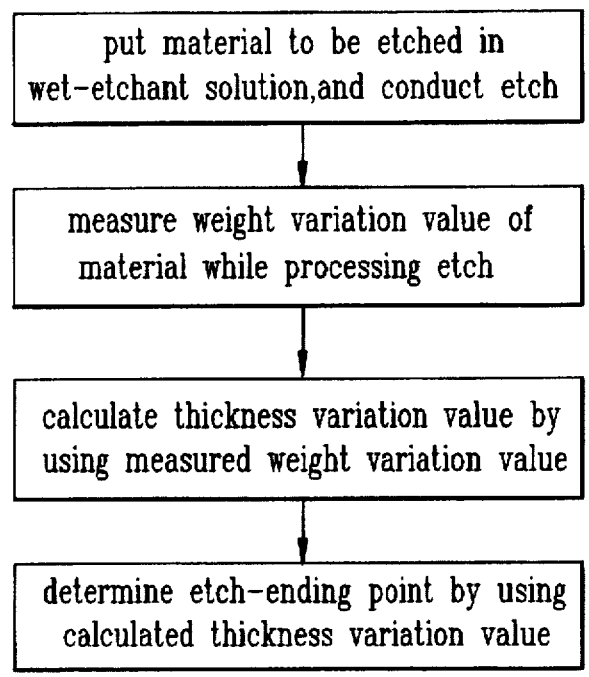
FIG. 1 is a block diagram showing an etch-ending point measuring method for a wet etch process according to the present invention.

Reference will now be made in detail to the preferred embodiments of the present invention, examples of which are illustrated in the accompanying drawings.

As described above, during the manufacturing process of a semiconductor device, a semiconductor layer, an insulating layer, or a conductive layer of a metal is usually subjected to a wet etch process.

In the present invention, hydrogen fluoride (HF), $H_3PO_4$, $NH_4OH$ or $H_2SO_4$ can be used as a wet-etchant. One common characteristic of all the wet-etchants listed above is their capability of releasing hydrogen ions ($H^+$). The hydrogen ions are formed in the etchant solution during the wet-etch process.

For discussion purpose, let us assume that a structure with a silicon oxide layer ($SiO_2$) formed on a silicon substrate is dipped into a HF solution, and the silicon oxide layer is subjected to a wet-etch process. The process of wet-etching the silicon oxide layer using the HF solution is expressed as the following reaction formula:

$$SiO_2 + 6HF \rightarrow 1H^+ + SiF_6^- + 2H_2O \qquad (1)$$

In accordance with the reaction formula (1), the hydrogen ion ($H^+$) of 6 mole before the reaction is changed to the hydrogen ion ($H^+$) of 2 mole after the reaction.

Because the mole-change of the hydrogen ion in the solution, the pH value of the etchant solution changes during the wet etch process, resulting a changing $\Delta pH$ value in accordance with an etch rate of the silicon oxide layer. As shown in reaction formula (1), the hydrogen ion ($H^+$) generally reacts with fluoride (F) to form $HF_2^-$ ion or remains unchanged in the etchant solution during the wet etch process. The pH value stops changing after the etch-ending point is reached, because the reaction in accordance with the reaction formula (1) stops when the desired etch upon the silicon oxide layer is completed and the surface of a silicon substrate is exposed. At this stage, the hydrogen ion ($H^+$) serves the purpose of passivating the surface of the silicon substrate.

As a result, when the wet etch is performed by using the hydrogen fluoride only, the etch rate (or etch speed) of the silicon oxide layer may change because the changing pH value. This is undesirable because it is difficult to accurately wet-etch the silicon oxide layer to the desired thickness when the etch rate changes.

Thus, a buffered etchant solution is often used for decreasing the variation of the etch rate caused by the changing pH value. For example, a buffered HF (BHF) solution (obtained by adding $NH_4F$ to the HF solution) can be used as a buffered etchant solution for etching the silicon oxide layer in the present invention.

During the wet-etch by using the BHF solution, the hydrogen ion ($H^+$) of the reaction formula (1) reacts with $NH_4F$ solution as in the following reaction:

$$H^+ + NH_4F \rightarrow NH_4^+ + HF \qquad (2)$$

Since the hydrogen ion of the reaction formula (1) becomes the hydrogen fluoride (HF) as expressed in the reaction formula (2), the pH value of the wet-etchant solution is not changed when the buffered etchant solution is used. Accordingly, the etch speed of the silicon oxide layer does not change during the etch process.

The present invention preferably uses a buffered etchant solution, such as a buffered HF (BHF) solution, a buffered $H_2PO_4$ solution ($BH_3PO_4$) or a buffered $NH_4OH$ solution ($BNH_4OH$). In addition, HF, $H_3PO_4$ or $NH_4OH$ solution which is not buffered may also be used.

In the etch-ending point measuring method according to the present invention as shown in the process of FIG. 1, a material subjected to etching is dipped into the wet-etchant solution filled in a bath. After a period of time, a weight variation value $\Delta w$ of the material to be etched is measured during the wet-etch. Then, the measured weight variation value $\Delta w$ is used to calculate a thickness variation value $\Delta T$ of the material being etched. Finally, the calculated thickness variation value $\Delta T$ is used for determining the etch-ending point.

As an example, the etch-ending point measuring method according to the present invention will be described in detail by using the silicon oxide layer ($SiO_2$) as the material to be etched, and it is assumed that the silicon oxide layer to be etched is formed on a silicon substrate.

Figure 2:
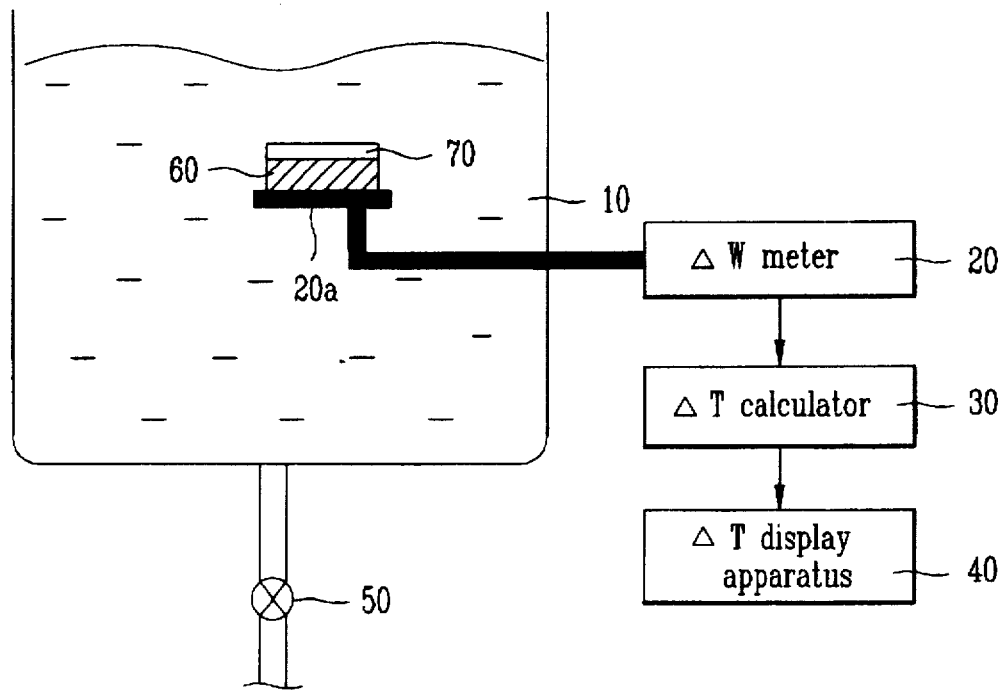
FIG. 2 is a schematic construction view showing a wet-etch apparatus for embodying the etch-ending point measuring method according to the present invention.

FIG. 2 is a schematic block diagram showing the wet-etch apparatus embodying the etch-ending point measuring method according to the present invention. In FIG. 2, a reference numeral 10 denotes a bath for retaining the wet-etchant solution; 20 is a $\Delta w$ meter with a stage 20a attached; 30 is a $\Delta T$ calculator; 40 is a $\Delta T$ display apparatus; 50 is a valve for controlling the supply of the wet-etchant solution; 60 is the silicon substrate; and 70 is the silicon oxide layer subjected to the etch.

Here, the $\Delta w$ meter 20 is a microbalance of any weight measuring apparatus providing that it has a calibration region capable of measuring the weight variation value $\Delta w$ of the silicon oxide layer 70.

Initially, a proper amount of the BHF solution is filled in the bath 10 via the valve 50 as the wet-etchant solution, and the silicon oxide layer 70 (formed on silicon substrate 60) to be etched is dipped into the BHF solution and put on the stage 20a of the $\Delta w$ meter 20. As the wet etch is conducted and the reaction is performed in conformity with the reaction formulas (1) and (2), the $\Delta w$ meter 20 continuously or discretely measures the weight variation value $\Delta w$ of the silicon oxide layer 70. The absolute value of the weight variation value $\Delta w$ is zero initially and then gradually increases as the wet-etch proceeds.

The $\Delta T$ calculator 20 then uses the weight variation value $\Delta w$ of the silicon oxide layer 70 to calculate the etched thickness of the silicon oxide layer 70, i.e., the thickness variation value $\Delta T$. The calculation process will now be described.

If an open area of the silicon oxide layer 70 subjected to the etch is A ($cm^2$), a density value of the material to be etched is $\rho$ ($g/cm^3$) ($\rho$ for the silicon oxide Layer 70 is 2.2 $g/cm^3$), the $\Delta T$ calculator 30 calculates the thickness variation value $\Delta T$ (cm) of the silicon oxide layer 70 as the following:

$$\Delta T = \Delta w \times 1/\rho \times 1/a \qquad (3)$$

The density $\rho$ (often a well-known value) and the area A subjected to the etch are pre-set in the $\Delta T$ calculator 30.

When the silicon oxide layer 70 is etched within the bath 10, the $\Delta T$ display apparats 40 continuously or discretely displays the $\Delta T$ value for that particular moment. The wet-etch process is stopped when the $\Delta T$ value displayed by the $\Delta T$ display apparatus 40 reaches a desired value corresponding to the etch-ending point.

The present invention may also be applied to the wet etch of other types of insulating layer (for example, a silicon nitride layer), a semiconductor layer such as a polysilicon layer, or a conductive layer of a metal. In etching the polysilicon layer, a sulfuric acid ($H_2SO_4$) solution is used as the etchant solution.

The present invention has the following advantages. First, since the present invention is an automatic etch-ending point measuring method instead of a visual measuring method, it allows the wet etch process to be performed within a shorter period of time than the conventional methods.

Second, the present invention is cost effective because an enlarged test pattern area is not required. This prevents unnecessary consumption of the chemical solution and the etched material.

This, the etch-ending point is measured more accurately in the present invention than the conventional methods, thus preventing possible failures during the wet etch.

It will be apparent to those skilled in the art that various modifications and variations can be made in the etch-ending point measuring method of the present invention without departing from the spirit or scope of the invention. Thus, it is intended that the present invention cover the modifications and variations of this invention provided they come within the scope of the appended claims and their equivalents.

What is claimed is:

1. A wet-etching method which determines a desired etch-ending point comprising the steps of:
   providing an etchant solution in a bath;
   performing a wet-etch process by dipping a material to be etched in the bath;
   measuring a weight variation value of the material during the wet etch process while the material is immersed in the etchant solution;
   calculating a thickness variation value of the material by using the weight variation value; and
   stopping the wet-etch process when the thickness variation value reaches a preset value.

2. The wet-etching method as claimed in claim 1, wherein the material subjected to the wet-etch process comprises an insulating layer.

3. The wet-etching method as claimed in claim 2, wherein the insulating layer comprises a silicon oxide layer.

4. The wet-etching method as claimed in claim 2, wherein the insulating layer comprises a silicon nitride layer.

5. The wet-etching method as claimed in claim 2, wherein the etchant solution includes one of a HF solution, a $H_3PO_4$ solution, a $NH_4OH$ solution, a buffered HF solution, a buffered $H_3PO_4$ solution, and a buffered $NH_4OH$ solution.

6. The wet-etching method as claimed in claim 1, wherein the material subjected to the wet-etch process comprises a semiconductor layer and the etchant solution comprises an acid solution.

7. The wet-etching method as claimed in claim 6, wherein the etchant solution comprises a $H_2SO_4$ solution.

8. The wet-etching method as claimed in claim 6, wherein the material comprises polysilicon.

9. The wet-etching method as claimed in claim 1, wherein the step of calculating the thickness variation value is performed by dividing the weight variation value with a density value of the material and an open area of the material subjected to the wet-etch process.

10. The wet-etching method as claimed in claim 1, wherein the weight variation value is measured continuously.

11. The wet-etching method as claimed in claim 1, wherein the weight variation value is measured discretely.

12. An etch-ending point measuring method for a wet-etch process comprising the steps of:
    measuring a weight variation value of a material to be etched during the wet etch process while the material is immersed in an etchant solution;
    calculating a thickness variation value of the material by using the weight variation value; and determining an etch-ending point when the calculated thickness variation value reaches a preset value.

13. The etch-ending point measuring method as claimed in claim 12, wherein the material to be etched comprises an insulating layer.

14. The etch-ending point measuring method as claimed in claim 13, wherein the insulating layer comprises a silicon oxide layer.

15. The etch-ending point measuring method as claimed in claim 13, wherein the insulating layer comprises a silicon nitride layer.

16. The etch-ending point measuring method as claimed in claim 13, wherein the etchant solution includes one of a HF solution, a $H_3PO_4$ solution, a $NH_4OH$ solution, a buffered HF solution, a buffered $H_3PO_4$ solution, and a buffered $NH_4OH$ solution.

17. The etch-ending point measuring method as claimed in claim 12, wherein the material to be etched comprises a semiconductor layer and the etchant solution comprises an acid solution.

18. The etch-ending point measuring method as claimed in claim 17, wherein the etchant solution comprises a $H_2SO_4$ solution.

19. The etch-ending point measuring method as claimed in claim 17, wherein the material comprises polysilicon.

20. The etch-ending point measuring method as claimed in claim 12, wherein the weight variation value is measured continuously.

21. The etch-ending point measuring method as claimed in claim 12, wherein the weight variation value is measured discretely.

* * * * *